US011657547B2

(12) United States Patent
Nagata

(10) Patent No.: US 11,657,547 B2
(45) Date of Patent: May 23, 2023

(54) ENDOSCOPIC SURGERY SUPPORT APPARATUS, ENDOSCOPIC SURGERY SUPPORT METHOD, AND ENDOSCOPIC SURGERY SUPPORT SYSTEM

(71) Applicant: Ziosoft, Inc., Tokyo (JP)

(72) Inventor: Tsuyoshi Nagata, Tokyo (JP)

(73) Assignee: ZIOSOFT, INC., Tokyo (JP)

( * ) Notice: Subject to any disclaimer, the term of this patent is extended or adjusted under 35 U.S.C. 154(b) by 149 days.

(21) Appl. No.: 17/021,174

(22) Filed: Sep. 15, 2020

(65) Prior Publication Data
US 2021/0082164 A1 Mar. 18, 2021

(30) Foreign Application Priority Data

Sep. 18, 2019 (JP) .............................. JP2019-169671

(51) Int. Cl.
*G06T 11/00* (2006.01)
*G06T 7/70* (2017.01)
(Continued)

(52) U.S. Cl.
CPC ............ *G06T 11/008* (2013.01); *A61B 34/10* (2016.02); *G06T 7/0012* (2013.01); *G06T 7/11* (2017.01);
(Continued)

(58) Field of Classification Search
CPC .............. A61B 34/10; A61B 2034/105; A61B 2034/107; G06T 7/0012; G06T 7/11;
(Continued)

(56) References Cited

U.S. PATENT DOCUMENTS 8,311,300 B1 11/2012 Matsumoto
9,761,014 B2 * 9/2017 Oktay ....................... G06T 7/33
(Continued)

FOREIGN PATENT DOCUMENTS

JP 2014-054358 A 3/2014

OTHER PUBLICATIONS

Oktay et al. "Biomechanically driven registration of pre-to intra-operative 3D images for laparoscopic surgery." International Conference on Medical Image Computing and Computer-Assisted Intervention. Springer, Berlin, Heidelberg, 2013. (Year: 2013).*

(Continued)

*Primary Examiner* — Katrina R Fujita
(74) *Attorney, Agent, or Firm* — Pearne & Gordon LLP

(57) ABSTRACT

An apparatus includes: an acquisition circuit; and a processing circuit configured to: acquire volume data; set a model representing a tissue included in the volume data; set a first view for visualizing the volume data and a position of a target in the model; acquire first operation information for deforming the model; calculate change in the position and an orientation of the target due to deformation of the model, based on the first operation information; calculate, using the calculated change in the position and the orientation of the target, a second view such that the position and the orientation of the target after the change with respect to the first view and the position and the orientation of the target before the change with respect to the second view become equal to each other; and visualize the volume data based on the second view.

9 Claims, 11 Drawing Sheets

(51) Int. Cl.
*G06T 7/11* (2017.01)
*G06T 7/00* (2017.01)
*A61B 34/10* (2016.01)

(52) U.S. Cl.
CPC .......... *G06T 7/70* (2017.01); *A61B 2034/105* (2016.02); *A61B 2034/107* (2016.02); *G06T 2207/10068* (2013.01); *G06T 2207/10081* (2013.01); *G06T 2207/30004* (2013.01)

(58) Field of Classification Search
CPC . G06T 7/70; G06T 7/75; G06T 11/008; G06T 2207/10068; G06T 2207/10081; G06T 2207/30004
See application file for complete search history.

(56) References Cited

U.S. PATENT DOCUMENTS

| | | | | |
|---|---|---|---|---|
| 11,062,527 | B2* | 7/2021 | Coustaud | G06T 19/00 |
| 2014/0071072 | A1 | 3/2014 | Itai | |
| 2015/0265369 | A1* | 9/2015 | Garbey | A61B 34/20 600/410 |
| 2018/0200002 | A1* | 7/2018 | Kostrzewski | G02C 7/049 |
| 2019/0350659 | A1* | 11/2019 | Wang | A61B 90/00 |

OTHER PUBLICATIONS

Bano et al. "Simulation of pneumoperitoneum for laparoscopic surgery planning." International Conference on Medical Image Computing and Computer-Assisted Intervention. Springer, Berlin, Heidelberg, 2012. (Year: 2012).*

Hayashi et al. "Development and clinical application of surgical navigation system for laparoscopic hepatectomy." Medical Imaging 2015: Image-Guided Procedures, Robotic Interventions, and Modeling. vol. 9415. International Society for Optics and Photonics, 2015. (Year: 2015).*

Nimura et al. "Pneumoperitoneum simulation based on mass-spring-damper models for laparoscopic surgical planning." Journal of Medical Imaging 2.4 (2015): 044004. (Year: 2015).*

Penza et al. "Dense soft tissue 3D reconstruction refined with super-pixel segmentation for robotic abdominal surgery." International journal of computer assisted radiology and surgery 11.2 (2016): 197-206. (Year: 2016).*

Takayuki Kitasaka, et al., "Virtual Pneumoperitoneum for Generating Virtual Laparoscopic Views Based on Volumetric Deformation", MICCAI (Medical Image Computing and Computer-Assisted Intervention), 2004, P559-P567.

* cited by examiner

ENDOSCOPIC SURGERY SUPPORT APPARATUS, ENDOSCOPIC SURGERY SUPPORT METHOD, AND ENDOSCOPIC SURGERY SUPPORT SYSTEM

CROSS-REFERENCE TO RELATED APPLICATIONS

This application is based on and claims priority under 35 USC 119 from Japanese Patent Application No. 2019-169671 filed on Sep. 18, 2019, the contents of which are incorporated herein by reference.

TECHNICAL FIELD

The present disclosure relates to an endoscopic surgery support apparatus, an endoscopic surgery support method, and an endoscopic surgery support system.

BACKGROUND ART

In the related art, in a surgical simulation, a medical image display device is known which performs processing on a three-dimensional medical image of a subject in accordance with an operation input on a display window and displays the processed three-dimensional medical image on the display window (refer to US20140071072A1). The processing on the three-dimensional medical image here includes deformation processing.

The medical image display device of US20140071072A1 has room for improvement in visualization of a target in a subject in intraoperative navigation or preoperative simulation.

The present disclosure has been made in view of the above-described circumstances, and provides an endoscopic surgery support apparatus, an endoscopic surgery support method, and an endoscopic surgery support system that are capable of improving visualization of a target in a subject.

SUMMARY

An endoscopic surgery support apparatus for supporting endoscopic surgery related to the present disclosure includes: an acquisition circuit; and a processing circuit configured to: acquire volume data of a subject; set a model that represents a tissue included in the volume data; set a first view for visualizing the volume data and a position of a target in the model; acquire first operation information for deforming the model; calculate change in the position and an orientation of the target due to deformation of the model, based on the first operation information; calculate, using the calculated change in the position and the orientation of the target, a second view such that the position and the orientation of the target after the change with respect to the first view and the position and the orientation of the target before the change with respect to the second view become equal to each other; and visualize the volume data based on the second view.

According to the present disclosure, it is possible to improve the easiness of making an observation environment of the target in the subject.

DESCRIPTION OF EMBODIMENTS

Figure 1:
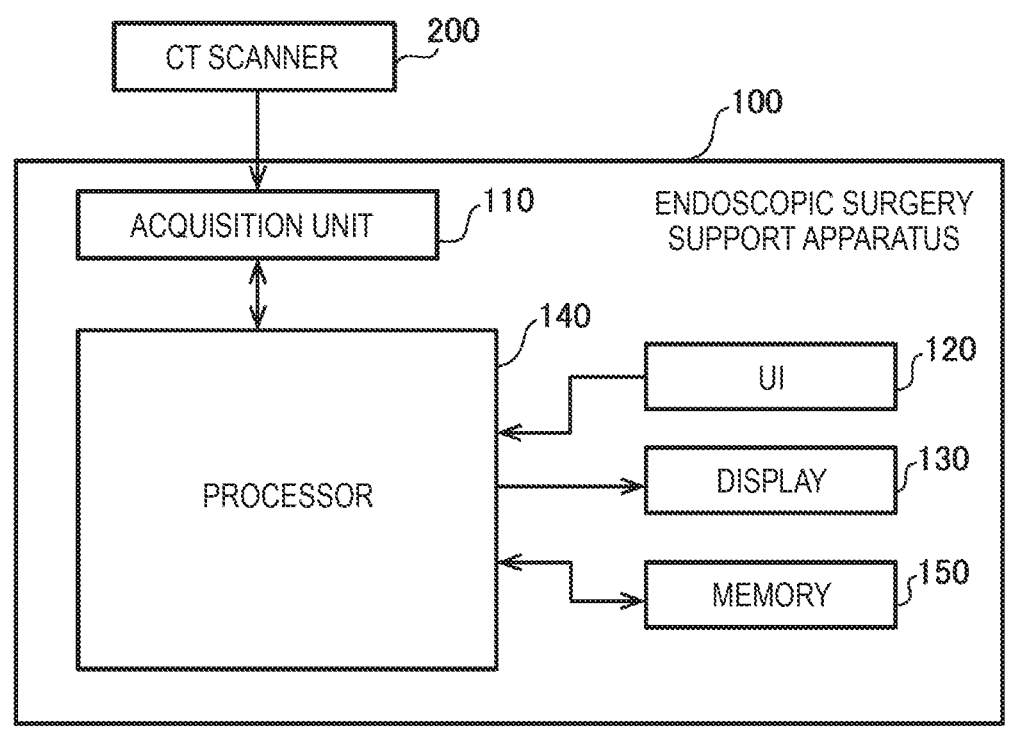
FIG. 1 is a block diagram illustrating a hardware configuration example of a medical image processing device according to a first embodiment.

Hereinafter, embodiments of the present disclosure will be described with reference to the drawings.
(Background of Obtaining One Aspect of Present Disclosure)

In preoperative simulation or intraoperative navigation, there is a case where a target which is a part of a subject is focused and observed in detail. For example, in endoscopic surgery, in a case where the target is positioned behind an organ when viewed from a camera position, it is considered to deform the organ such that the target can be confirmed from the camera position. In this case, in a case where the medical image display device of US20140071072A1 is used, a part of the organ in the volume data is deformed and a three-dimensional medical image is displayed on a display by volume rendering or the like. Therefore, deformation processing is performed with respect to the volume data, and is computationally demanding.

Furthermore, it is necessary to appropriately set the rigidity for each voxel of the volume data, and to consider the slippage at the boundary of the organ, the flow of body fluid, and the air. Further, in a case where the organ is repeatedly deformed little by little considering a surgery process, it is necessary to maintain the consistency of the volume data related to the deformation processing. Therefore, it becomes necessary to manually make fine adjustment with respect to the volume data and a region of interest. Therefore, for example, it is difficult to perform a real-time simulation in which an operator operates an organ using forceps in endoscopic surgery.

In addition, since the image that is deformed and rendered by non-rigid deformation processing of the volume data is confirmed as it is in the preoperative simulation and the intraoperative navigation, the accuracy of the deformation processing is required to be high. In particular, it is required that the organ boundaries are not broken.

In addition, in a case of deforming the organ, in order to make it easy to observe the organ that includes the target, visualization of the target after performing division (segmentation) processing in which other organs (for example, a small intestine in an abdominal region) in the neighbor of this organ are finely removed can also be considered, but this is a roundabout method. It is also possible to consider to perform a simulation in which only the organ that includes the target is deformed, but in this case, there is a possibility that a plurality of organs overlap each other in a virtual space, and the visualization accuracy of the subject may deteriorate.

Further, when surface data is deformed instead of the volume data, the processing speed related to the deformation can be improved, but the accuracy of the surface rendering may be insufficient. This is because, in a case where segmentation of each organ is inaccurate for generating the surface data, for example, when there are a large number of peripheral blood vessels, it is difficult to accurately generate the surface of the peripheral blood vessels or the complicated organ. For example, blood vessels that are connected to the liver and blood vessels that are not connected to the part may be more unclearly visualized.

In the following embodiments, an endoscopic surgery support apparatus, an endoscopic surgery support method, and an endoscopic surgery support system that are capable of improving visualization of a target in a subject will be described.

First Embodiment

FIG. 1 is a block diagram illustrating a configuration example of a medical image processing device 100 according to a first embodiment. The medical image processing device 100 includes an acquisition unit 110, a UI 120, a display 130, a processor 140, and a memory 150. The medical image processing device 100 supports endoscopic surgery (including robot surgery) by image processing. The medical image processing device 100 performs, for example, intraoperative navigation for performing support during surgery by an operator, or preoperative simulation for establishing an operation plan before surgery by the operator.

A CT scanner 200 is connected to the medical image processing device 100. The medical image processing device 100 acquires the volume data from the CT scanner 200 and processes the acquired volume data. The medical image processing device 100 may be configured of a PC and software installed in the PC.

The CT scanner 200 irradiates the subject with X-rays, and captures images (CT images) by using the difference in X-ray absorption by tissues in the body. The subject may include a living body, a human body, an animal, and the like. The CT scanner 200 generates the volume data including information on an arbitrary location on the inside of the subject. The CT scanner 200 transmits the volume data as the CT image to the medical image processing device 100 via a wired circuit or a wireless circuit. Imaging conditions for CT images and contrast conditions for administration of a contrast medium may be taken into consideration when capturing CT images.

The acquisition unit 110 in the medical image processing device 100 includes, for example, a communication port, an external device connection port, and a connection port to an embedded device, and acquires the volume data obtained by the CT scanner 200. The acquired volume data may be immediately sent to the processor 140 for various types of processing, or may be sent to the processor 140 for various types of processing when necessary after storing the volume data in the memory 150. Further, the volume data may be acquired via a recording medium or a storage media. In addition, the volume data may be acquired in the form of intermediate data, compressed data or sinogram. Further, the volume data may be acquired from information from a sensor device attached to the medical image processing device 100. In this manner, the acquisition unit 110 has a function of acquiring various types of data such as volume data.

The UI 120 may include, for example, a touch panel, a pointing device, a keyboard, or a microphone. The UI 120 receives an arbitrary input operation from the user of the medical image processing device 100. Users may include operators, doctors, nurses, radiologists, students, and the like.

The UI 120 receives various operations. For example, an operation, such as designation of a region of interest (ROI) or setting of a brightness condition, in the volume data or in an image (for example, a three-dimensional image or a two-dimensional image which will be described later) based on the volume data, is received. The ROI may include regions of various tissues (for example, blood vessels, bronchi, organs, viscera, bones, and brain). The tissue may include diseased tissue, normal tissue, tumor tissue, and the like. In addition, the UI 120 may receive various operations (for example, deforming operation) on the model generated based on the volume data.

The display 130 may include an LCD, for example, and displays various types of information. The various types of information may include a three-dimensional image and a two-dimensional image obtained from the volume data. The three-dimensional images may include a volume rendering image, a surface rendering image, a virtual endoscopic image, a virtual ultrasound image, a CPR image, and the like. The volume rendering images may include a RaySum image, an MIP image, an MinIP image, an average value image, a raycast image, and the like. The two-dimensional images may include an axial images, a sagittal image, a coronal image, an MPR image, and the like.

The memory 150 includes various primary storage devices such as ROM and RAM. The memory 150 may include a secondary storage device such as HDD or SSD. The memory 150 may include a tertiary storage device such as a USB memory or an SD card. The memory 150 stores various types of information and programs. The various types of information may include volume data acquired by the acquisition unit 110, images generated by the processor 140, setting information set by the processor 140, and various programs. The memory 150 is an example of a non-transitory recording medium on which a program is recorded.

The processor 140 may include a CPU, a DSP, or a GPU. The processor 140 functions as a processing unit 160 that performs various types of processing and controls by executing the medical image processing program stored in the memory 150.

Figure 2:
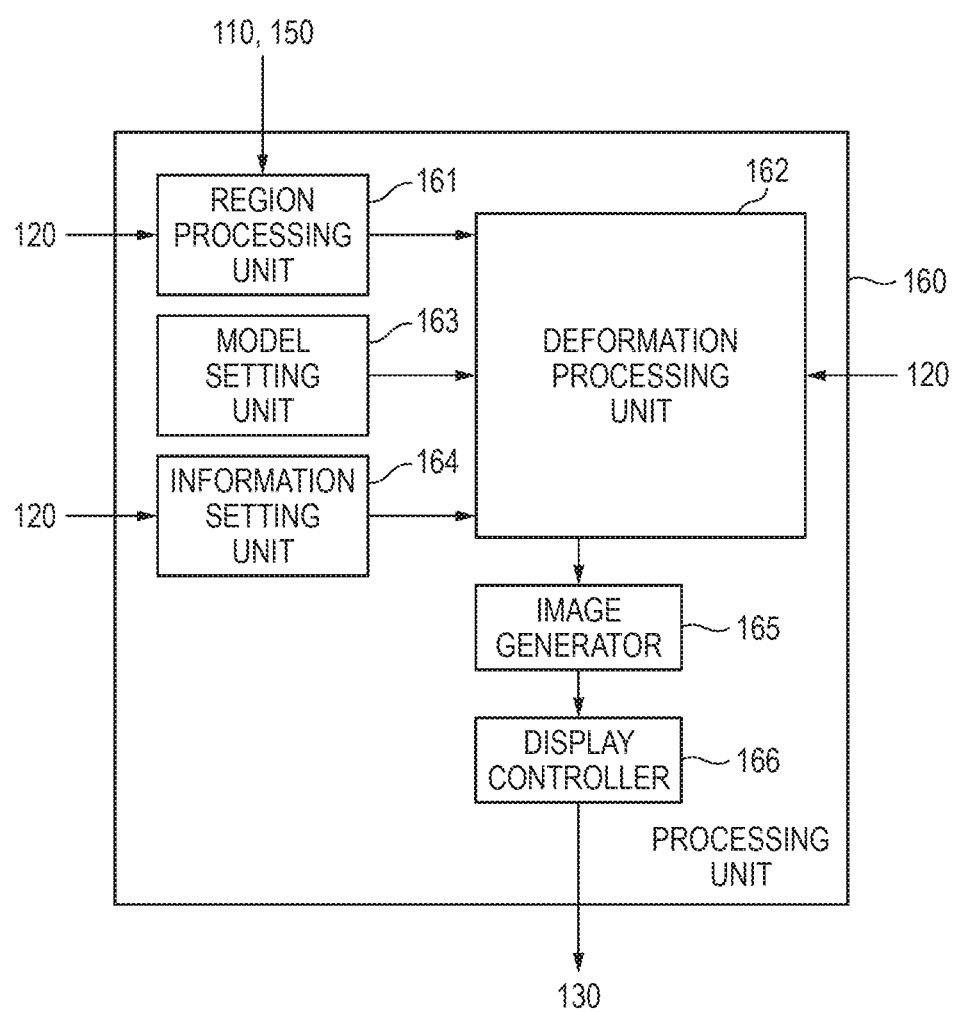
FIG. 2 is a block diagram illustrating a functional configuration example of the medical image processing device.

FIG. 2 is a block diagram illustrating a functional configuration example of the processing unit 160. The processing unit 160 includes a region processing unit 161, a deformation processing unit 162, a model setting unit 163, an information setting unit 164, an image generator 165, and a display controller 166. Each unit included in the processing unit 160 may be realized as different functions by one piece of hardware, or may be realized as different functions by a plurality of pieces of hardware. In addition, each unit included in the processing unit 160 may be realized by a dedicated hardware component.

The region processing unit 161 acquires the volume data of the subject via the acquisition unit 110, for example. The region processing unit 161 extracts an arbitrary region included in the volume data. The region processing unit 161 may automatically designate the ROI and extract the ROI based on a pixel value of the volume data, for example. The region processing unit 161 may manually designate the ROI and set the ROI via the UI 120, for example. The ROI may include regions such as organs, bones, blood vessels, affected parts (for example, diseased tissue or tumor tissue).

Further, the ROI may be segmented and extracted, including not only a single tissue but also tissues around the tissue. For example, in a case where the organ as the ROI is the liver, not only the liver itself but also blood vessels (for example, hepatic artery, hepatic vein, and portal vein) that are connected to the liver or travel in or in the neighbor of the liver, and bones (for example, backbone and rib bone) in the neighbor of the liver may be included. Further, the above-described liver itself, the blood vessels in or in the neighbor of the liver, and the bones in the neighbor of the liver may be segmented and obtained as separate tissues.

The model setting unit 163 sets a model of the tissue. The model may be set based on the ROI and the volume data. The model represents the tissue visualized by the volume data in a simpler manner than the volume data. Therefore, the data amount of the model is smaller than the data amount of the volume data corresponding to the model. The model is a target of the deformation processing and the deforming operation. The model may be, for example, a bone deformation model. In this case, the model deforms the bone by assuming a frame in a simple finite element and moving the vertices of the finite element. The deformation of the tissue can be represented by following the deformation of the bone. The model may include an organ model imitating an organ (for example, a liver). The model may have a shape similar to a simple polygon (for example, a triangle), or may have other shapes. The model may be, for example, a contour line of the volume data indicating an organ. The model may be a three-dimensional model or a two-dimensional model. In addition, the bone may be represented by the deformation of the volume data instead of the deformation of the model. This is because, since the bone has a low degree of freedom of deformation, it is possible to represent by affine deformation of the volume data.

The model setting unit 163 may acquire the model by generating the model based on the volume data. Further, a plurality of model templates may be predetermined and stored in the memory 150 or an external server. The model setting unit 163 may acquire a model by acquiring one model template among a plurality of model templates prepared in advance from the memory 150 or the external server according to the volume data.

The information setting unit 164 inputs or acquires and sets various types of information. For example, the information setting unit 164 may set information (camera information) regarding the endoscope (camera) used in the endoscopic surgery. The camera is inserted from the camera port and images the inside of the subject. The camera information may include information such as a camera position with respect to the subject, a camera orientation, and a camera angle of view. The camera orientation is the orientation in which the camera captures an image, and may coincide with the direction of the optical axis of the camera. The imaging range of the camera may be determined in accordance with the camera position, the camera orientation, and the camera angle of view. In other words, the camera position can also be said to be a camera of the operator for observing the subject. The camera orientation can also be said to be the orientation of the line of sight of the operator starting from the camera. The camera angle of view can also be said to be an angle of visibility of the operator based on the camera. The imaging range can also be said to be the view of the operator. The view may be determined in accordance with the camera, the orientation of the line of sight, and the angle of visibility. The view serves as a standard for visualizing the volume data. In addition, the camera position, the camera orientation, the camera angle of view, and the imaging range here are information that has considered the camera that is actually disposed, and thus, are also referred to as the actual camera position (actual camera), the actual camera orientation (actual orientation of line of sight), the actual camera angle of view (actual angle of visibility), and the actual imaging range (actual view). The actual camera information here is also referred to as actual camera information. The information setting unit 164 may acquire and set the camera information detected by an arbitrary sensor in the intraoperative navigation.

The information setting unit 164 sets forceps information regarding forceps (actual forceps) operated by the operator. The forceps information may include information on the position and the orientation of the forceps.

The information setting unit 164 may set information on the positions of various ports to be punched in the subject. The various ports include, for example, a forceps port into which forceps are inserted and a camera port into which a camera is inserted. Since the camera is inserted from the camera port, the degree of freedom of movement is small. Moreover, since the forceps are inserted from the forceps port, the degree of freedom of movement is small.

The information setting unit 164 sets the target information on the target in the model corresponding to the tissue by simulating the target in the tissue. The target information may include information on the position and the orientation of the target. The target is set in an arbitrary tissue (for example, an organ) or in the vicinity of the tissue. When the target position is determined, the orientation of the target (target orientation) is determined. The target orientation is a parameter used to obtain the change in the orientation of the target during deformation, and the initial value can be set arbitrarily. The target position can be in a tangential direction at the position of the target within the tissue or a point on the contour of the tissue having the shortest distance from the target position within the tissue. The information setting unit 164 may designate the target position via the UI 120. In addition, the position of the target (for example, affected part) treated in the past in the subject may be stored in the memory 150. The information setting unit 164 may acquire and set the target position from the memory 150. The information setting unit 164 may calculate and set the target orientation based on the target position in the tissue.

The deformation processing unit 162 performs processing related to the deformation in the subject which is a surgery target. Tissues such as organs in the subject can be subjected to various deforming operations by the user by simulating various treatments performed by the operator in surgery. The deforming operation may include an operation of lifting an organ, an operation of flipping an organ, an operation of cutting an organ, and the like. In response to this, the deformation processing unit 162 may deform the model corresponding to the tissue such as the organ in the subject as the processing related to the deformation. For example, an organ may be pulled, pushed, or cut by forceps (for example, gripping forceps, peeling forceps, or an electric scalpel), but this situation may be simulated by the deformation of the model. These deformations may be executed, for example, so as to make a target, which is invisible or difficult to be seen by the operator by being positioned inside or behind the organ, visible (can be imaged) from the camera (corresponding to the camera position) of the operator. In other words, these deformations may be executed so as to make a target, which is invisible or difficult to be seen by the operator by being positioned inside or behind the model, visible from the camera of the operator. For example, the deformation causes a situation in which an obstacle (for example, a bone) is absent between the camera of the operator and the target. When the model deforms, the targets in the model may also deform.

The deformation by the deforming operation may be performed on the model and may be a large deformation simulation using the finite element method. For example, movement of an organ due to body posture change may be simulated. In this case, the elastic force applied to the contact point of the organ or the lesion, the rigidity of the organ or the lesion, and other physical characteristics may be taken into consideration. In the deformation processing on the model, the compute demand is reduced as compared with the deformation processing on the volume data. This is because the number of elements in the deformation simulation is reduced.

In setting of the model, information indicating which part of the modeled organ is connected to the other part of the subject, and information, whether the root part of the blood vessel connected to the organ (the part connected to the organ) is difficult to move, whether the tip part of the blood vessel is easy to move, whether the bone is difficult to move, whether other tissues move while avoiding bone, and the like can be set. The information indicating which part of the tissue is easy to move and difficult to move may be set individually in detail, for example, or may be set as uniform ease of movement. Moreover, the direction in which the tissue bends due to the deformation may be one or plural. In a case where the target exists behind the vein when viewed from the camera position, the deformation processing unit 162 can provide information indicating that it is difficult to deform the model such that the target is visible and the endoscopic surgery is difficult.

The model may be displayed on the display 130. The deformation processing unit 162 may deform the model by acquiring information on a deforming operation for the model via the UI 120. In this case, the deformation amount of each part in the model may be determined in accordance with the deforming operation amount for the model. The information on the deforming operation may include information of pushing the organ with forceps, for example. The information of pushing the organ may include information such as a position for pushing the organ, a force for pushing the organ, a direction for pushing the organ, and the like. The force for pushing the organ acts as a factor that deforms the movable point of the organ in the direction of pushing the organ.

The deformation processing unit 162 may limit the deformation of the model of the organ that includes the target in accordance with the positional relationship between the organ that includes the target and the organ that does not include the target. For example, in a case where there is a bone that is difficult to deform at the part around the organ, the bone may not be deformed, and there may be limitation such that the organ does not deform in the direction in which the bone exists. The limitation information regarding the limitation on the deformation of the model (for example, the information on the position where the deformation in the model is limited) may be set as the information on the model and stored in the memory 150.

The shape of the model may be inaccurate as compared with the actual tissue. For example, the contour of the organ may be inaccurate. Further, the degree of deformation of the model may be inaccurate as compared with the actual deformation of the tissue, and for example, the contour and shape before and after deformation of the organ may be inaccurate. For example, an incorrect contour at the end portion of the liver may allow a part of the stomach to enter the liver. This is because, even when the deformation of the model is slightly different from the actual deformation, it is sufficient when the target is easily visually recognized in the visualization of the volume data corresponding to the model.

The deformation processing unit 162 calculates changes in the target position and the target orientation before and after deformation of the model. In this case, the deformation of the model may be taken into consideration, and the target position and the target orientation after deformation may be calculated based on the target position and the target orientation before deformation.

The deformation processing unit 162 calculates a virtual camera position, a camera orientation, a camera angle of view, and an imaging range for visualizing the volume data. The camera position, the camera orientation, the camera angle of view, and the imaging range here are not information that has considered the camera that is actually disposed, but information which is virtually derived, and thus, are also referred to as the virtual camera position (virtual camera), the virtual camera orientation (virtual orientation of line of sight), the virtual camera angle of view (virtual angle of visibility), and the virtual imaging range (virtual view). The camera information which is virtual here is also referred to as virtual camera information.

The deformation processing unit 162, for example, calculates the virtual camera position and the virtual camera orientation for visualizing the target based on the actual camera position, the actual camera orientation, and the target position or the target orientation in the deformed (after deformation) organ. In this case, an angle A1 (refer to FIG. 3) formed by the target orientation of the organ after deformation including the target and the actual camera orientation is calculated. Then, the virtual camera position is determined such that an angle A2 (refer to FIG. 3) formed by the target orientation and the virtual camera orientation of the organ which is not deformed (before deformation) is the same as the calculated angle A1.

The deformation processing unit 162 may change the position and the orientation of the forceps in accordance with the deformation of the model. In this case, in a method similar to the change from the actual camera position and the actual camera orientation to the virtual camera position and the virtual camera orientation, the actual forceps position and the actual forceps orientation may be changed to the virtual forceps position and the virtual forceps orientation. For example, the virtual forceps position and the virtual forceps orientation may be calculated based on the actual forceps position, the actual forceps orientation, and the target position or the target orientation in the organ after deformation. In this case, the angle formed between the target orientation of the organ after deformation including the target and the actual forceps orientation may be calculated, and the virtual forceps position may be determined such that the angle formed by the target orientation of the organ before deformation and the virtual forceps orientation becomes the same as the calculated angle. In addition, the actual forceps may be considered as forceps at the time of actual surgery. The virtual forceps may be forceps virtually derived by computation.

Further, the deformation processing unit 162 may virtually perform a pneumoperitoneum simulation for pneumoperitoneum on the subject as processing related to the deformation. A specific method of pneumoperitoneum simulation may be a known method, for example, the method described in Reference Non-patent Literature 1. In other words, the deformation processing unit 162 may perform the pneumoperitoneum simulation based on the volume data in the non-pneumoperitoneum state and generate the volume data in the virtual pneumoperitoneum state. With the pneumoperitoneum simulation, the user can observe the virtual pneumoperitoneum state by assuming the pneumoperitoneum state of the subject even when there is no actual pneumoperitoneum in the subject. In addition, among the pneumoperitoneum states, a state of pneumoperitoneum estimated by the pneumoperitoneum simulation may be referred to as a virtual pneumoperitoneum state, and a state of actual pneumoperitoneum may be referred to as an actual pneumoperitoneum state.

(Reference Non-patent Literature 1) Takayuki Kitasaka, Kensaku Mori, Yuichiro Hayashi, Yasuhito Suenaga, Makoto Hashizume, and Jun-ichiro Toriwaki, "Virtual Pneumoperitoneum for Generating Virtual Laparoscopic Views Based on Volumetric Deformation", MICCAI (Medical Image Computing and Computer-Assisted Intervention), 2004, P559-P567

The pneumoperitoneum simulation may be a large deformation simulation using the finite element method. In this case, the deformation processing unit 162 may segment the body surface including the subcutaneous fat of the subject and the abdominal internal organs of the subject. Then, the deformation processing unit 162 may model the body surface as a two-layer finite element of skin and body fat, and model the abdominal internal organs as a finite element. The deformation processing unit 162 may arbitrarily segment, for example, lungs and bones and add the segmented result to the model. Further, a gas region may be provided between the body surface and the abdominal internal organs, and the gas region (pneumoperitoneum space) may be expanded (swollen) in accordance with virtual gas injection.

The image generator 165 generates various images. The image generator 165 generates a three-dimensional image or a two-dimensional image based on at least a part of the acquired volume data (for example, a region extracted in the volume data). The image generator 165 may generate a three-dimensional image or a two-dimensional image based on the volume data deformed by the deformation processing unit 162 (for example, the volume data in the virtual pneumoperitoneum state). In this case, the image generator 165 may generate a three-dimensional image or a two-dimensional image by visualizing (for example, rendering) the volume data so as to represent a state of viewing in the virtual camera orientation from the virtual camera position.

The display controller 166 causes the display 130 to display various types of data, information, and images. The image includes an image (for example, rendering image) generated by the image generator 165. The display controller 166 may also adjust the brightness of the rendered image. The brightness adjustment may include, for example, adjustment of at least one of a window width (WW: window width) and a window level (WL: window level).

Figure 3:
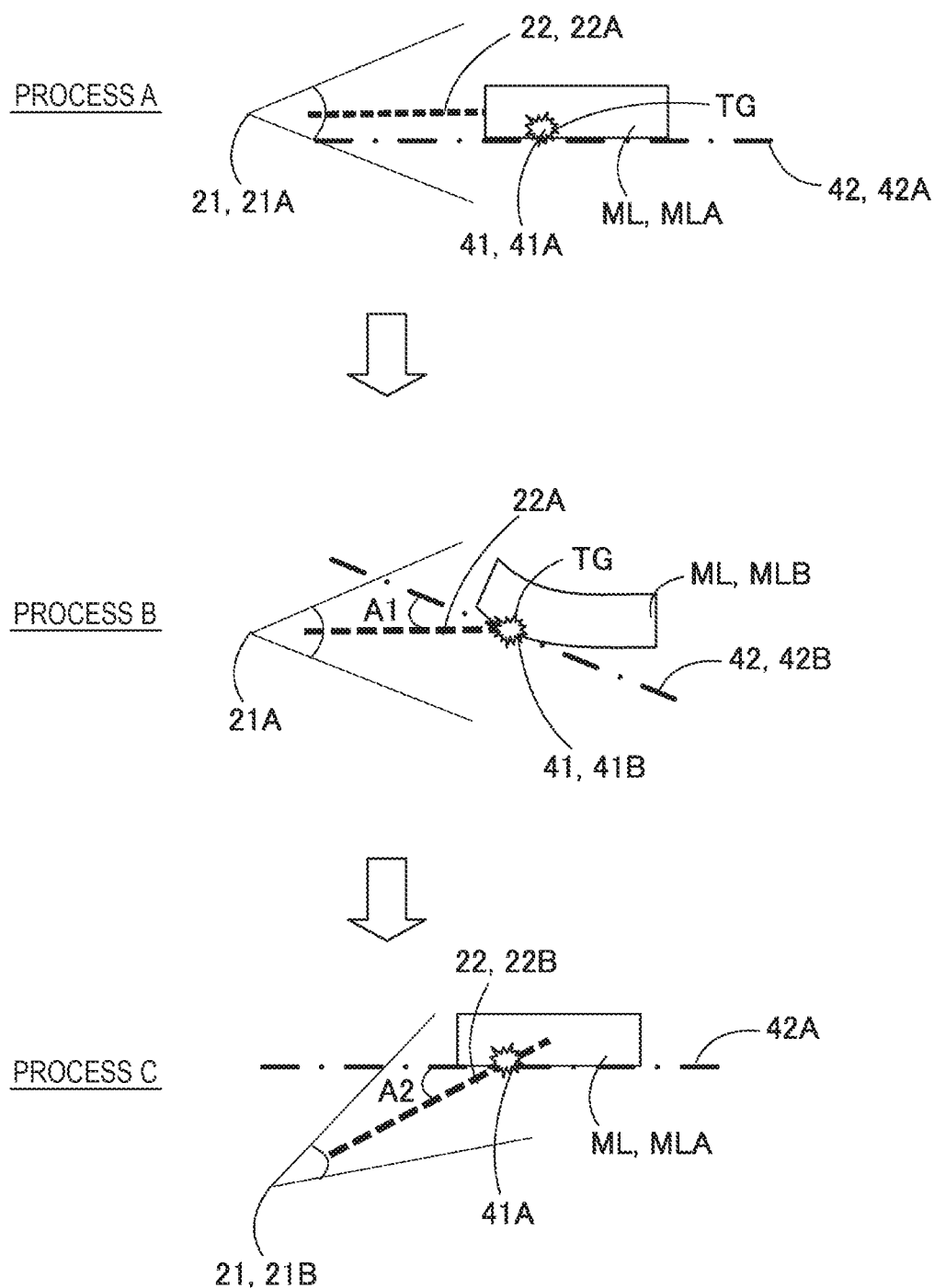
FIG. 3 is a view describing an overview of processing performed by the medical image processing device.

FIG. 3 is a view describing an overview of processing performed by the medical image processing device 100.

First, the acquisition unit 110 acquires the volume data of the subject. The region processing unit 161 extracts a region of an organ TL included in the subject as needed. The model setting unit 163 generates a model ML based on the region of the organ TL. A target TG is included in the organ TL (refer to process A, the organ TL will be described without distinction from the model ML). The model ML is a model MLA before deformation. In a state before deformation of the model ML, in a case where the organ TL corresponding to the model MLA is visualized as a situation of being viewed in an actual camera orientation 22A from an actual camera position 21A, the target TG cannot be visually recognized.

The deformation processing unit 162 performs deformation simulation on the model MLA to obtain a model MLB after deformation (refer to process B). In the deformation simulation, the deformation information is obtained. The deformation information may indicate, for example, the deformation of the bone of the model ML before and after deformation. Then, the deformation processing unit 162 calculates a target position 41B and a target orientation 42B after deformation. The target orientation 42 (42A, 42B) is a tangential direction at the target position 41 (41A, 41B) of the organ or the like. In a state of the model ML after deformation, in a case where the organ corresponding to the model MLB is visualized as a situation where the actual camera orientation 22A is viewed from the actual camera position 21A, the target TG of a lower portion of the organ TL is visible.

The information setting unit 164 acquires the actual camera information including the actual camera position 21A and the actual camera orientation 22A. The deformation processing unit 162 derives the positional relationship between the target after deformation and the actual camera based on the target position 41B and the target orientation 42B after deformation and the actual camera position 21A and the actual camera orientation 22A. The deformation processing unit 162 calculates the virtual camera position 21B and the virtual camera orientation 22B based on the positional relationship between the target after deformation and the actual camera, that is, based on the target position 41B and the target orientation 42B after deformation and the actual camera position 21A and the actual camera orientation 22A (refer to process C). In other words, the deformation processing unit 162 calculates the virtual camera position 21B and the virtual camera orientation 22B such that the angle and the distance at which the target TG should have been visible in the model MLB after deformation are achieved, in the model MLA before deformation. This angle indicates the angle A1 formed by the actual camera orientation 22A and the target orientation 42B after deformation, and the angle A2 formed by the virtual camera orientation 22B and the target orientation 42A before deformation, which are the same angle. The image generator 165 generates images visualized using the virtual camera position 21B and the virtual camera orientation 22B based on the volume data before deformation. The display controller 166 causes the display 130 to display the generated images. In other words, the original volume data before deformation is visualized based on the virtual camera information.

Accordingly, in the medical image processing device 100, in a state where the angular relationship between the actual camera and the target TG after deformation and the angular relationship between the virtual camera and the target TG before deformation are maintained, the organ including the target TG is visible from the virtual camera position 21B. Accordingly, the user can sufficiently observe the target TG. Therefore, as compared with a case where the target TG is visualized and observed by deforming the volume data of the organ and by making the target TG visible, the compute demand of the processor 140 and the labor of the user can be reduced. Even the visualization illustrating such an approach to the target TG is sufficient for the intraoperative navigation and the preoperative simulation.

Figure 4:
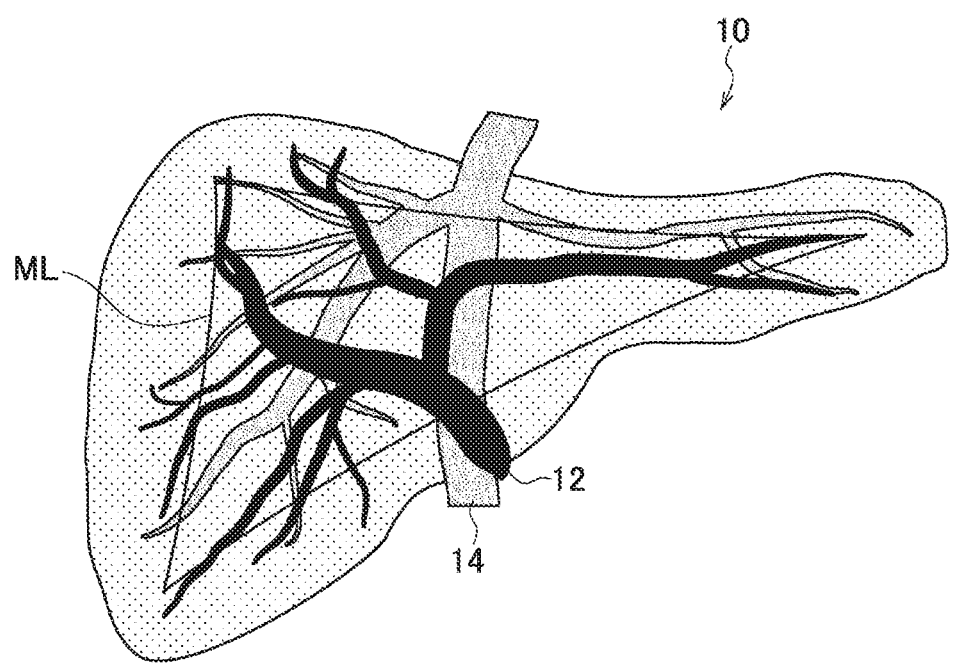
FIG. 4 is a view illustrating a generation example of a model.

FIG. 4 is a view illustrating a generation example of the model ML.

The model ML illustrated in FIG. 4 is a bone deformation model of the liver. The liver 10 includes a portal vein 12 and a vein 14. The region processing unit 161 segments and extracts the region including the liver 10 itself, the portal vein 12, and the vein 14 from the subject as the region of the liver 10. The liver 10 itself is connected to the portal vein 12 and the vein 14. The portal vein 12 and the vein 14 may be treated as fixation points outside the liver 10. This information is used, for example, when calculating the deformation of the bone using the finite element method. The liver 10 itself, the portal vein 12, and the vein 14 are extracted as separate regions, and the region obtained by combining these three regions may be considered as the region of the liver 10.

Figure 5:
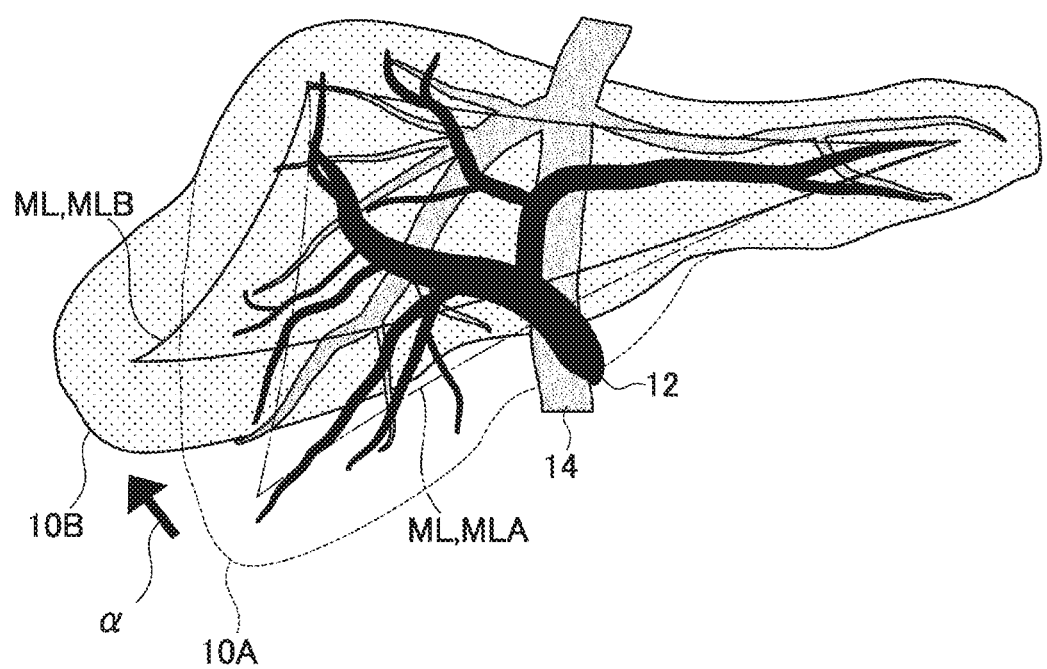
FIG. 5 is a view illustrating a deformation example of the model.

FIG. 5 is a view illustrating a deformation example of the model ML. The deformation processing unit 162 receives the deforming operation via the UI 120, for example, and deforms the model ML. For example, an operation of moving a part of the model MLA before deformation in the direction of an arrow a (upper left direction in FIG. 5) is received via the UI 120, the part of the model is deformed in the direction of the arrow a in accordance with the detection of this movement, and the model MLB after deformation is generated. A liver 10A illustrates the liver before deformation corresponding to the model MLA before deformation. A liver 10B illustrates the liver corresponding to the model MLB after deformation. Accordingly, the contour of the liver 10 changes before and after deformation. In addition, here, the model ML of the liver 10 is deformed, the volume data of the liver 10 is not deformed, and accordingly, the compute demand related to the deformation can be reduced.

Figure 6:
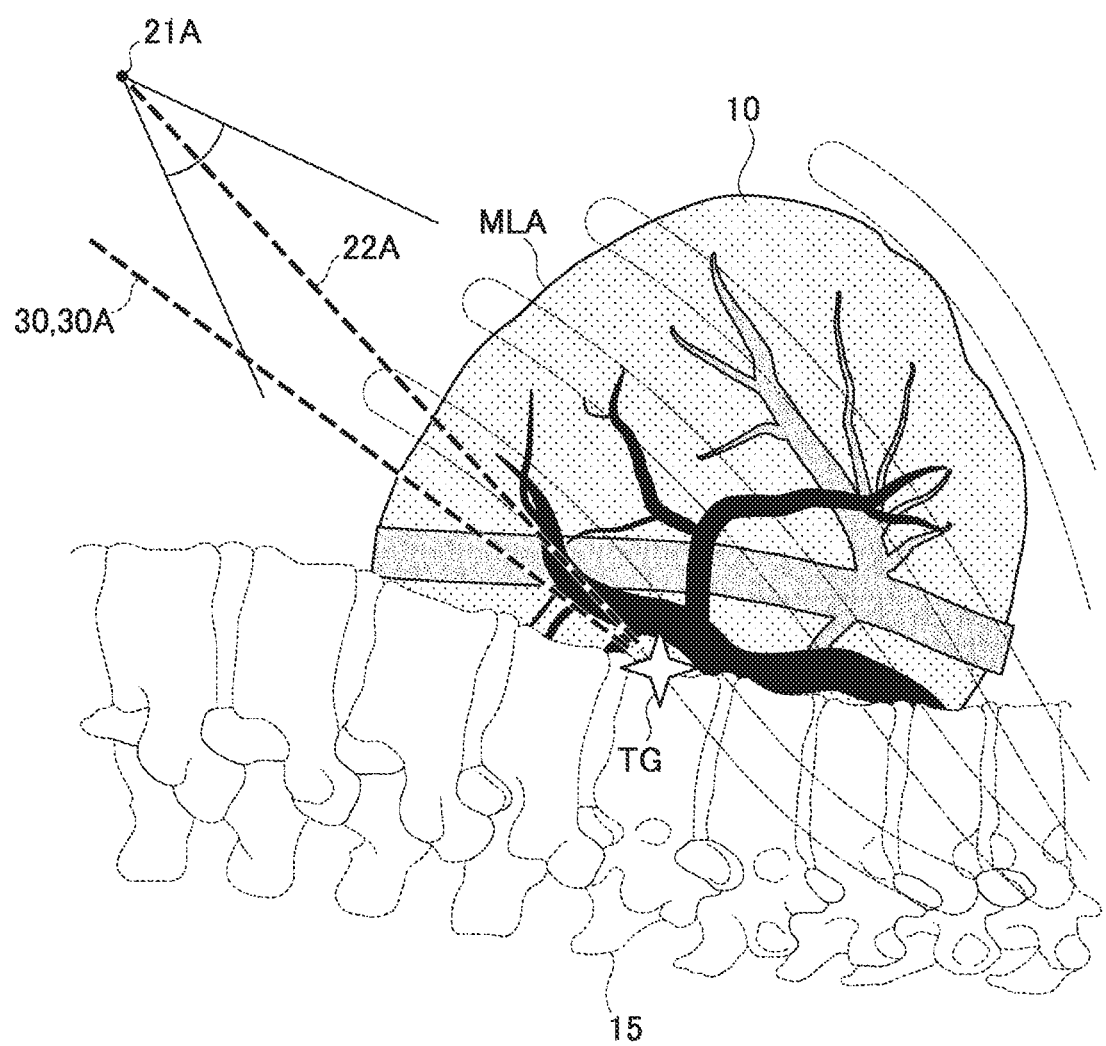
FIG. 6 is a schematic view illustrating an example of a positional relationship between a target and an actual camera position.

FIG. 6 is a schematic view illustrating an example of a positional relationship between the target TG and the actual camera position 21A. Here, laparoscopic surgery is taken as an example of the endoscopic surgery, but other endoscopic surgery may be performed. In addition, FIGS. 6 to 10 exemplify that the contour of the model ML coincides with the contour of the liver 10. The model ML may or may not be displayed on the display 130. FIGS. 6 to 10 exemplify that the model ML is an organ model of the liver 10.

In FIG. 6, the camera position (actual camera position 21A) and the camera orientation (actual camera orientation 22A) before deformation, and the position and the orientation of the forceps 30 are illustrated. In FIG. 6, when viewed from the actual camera position 21A, the target TG in the model MLA corresponding to the liver 10 before deformation is hidden behind the other locations of the liver 10. Therefore, the target TG cannot be confirmed even when viewing the actual camera orientation 22A from the actual camera position 21A. In addition, the positions of the actual camera position 21A and the forceps 30 do not coincide with each other and are different from each other.

Figure 7:
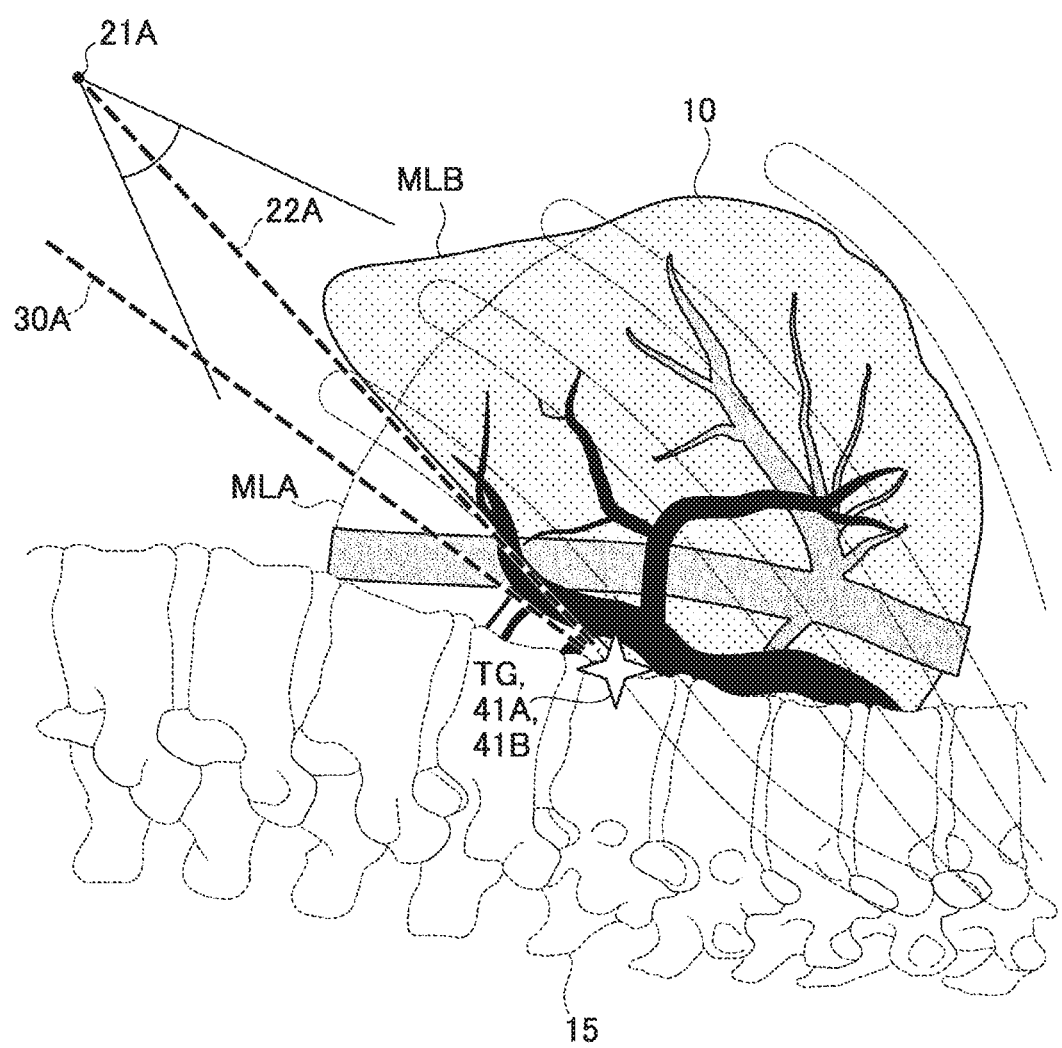
FIG. 7 is a schematic view illustrating the actual camera position and a deformation example of an organ.

FIG. 7 is a schematic view illustrating the actual camera position 21A and a deformation example of the organ.

The model MLA before deformation is deformed such that the target position 41 is visible from the camera position 21, that is, the obstacle is absent between the camera position 21 and the target position 41. The deformation of the model ML may be performed in accordance with the deforming operation via the UI 120. In the model MLB after deformation, the target position 41B is visible from the actual camera position 21A, that is, the obstacle is absent between the actual camera position 21A and the target position 41B. The obstacle here may be another location of the liver 10 including the target TG or another tissue (for example, bone).

Further, in FIG. 7, the target TG included in the model ML is deformed along with the deformation of the model ML corresponding to the liver 10, that is, the target position 41 or the target orientation 42 is changed. The deformation processing unit 162 may calculate movement information and rotation information before and after deformation of the target TG based on the deformation information related to the deformation of the model ML. For example, the operation of surgery by a user (for example, pulling an organ, flipping an organ, turning over an organ, and excising an organ) may be indicated by movement or rotation of the target TG due to deformation in computation. In other words, the deformation of the organ due to the surgical operation may be artificially represented by a combination of movement or rotation by computation. The deformation information of the model ML and the movement information or the rotation information of the target TG may be stored in the memory 150.

Figure 8:
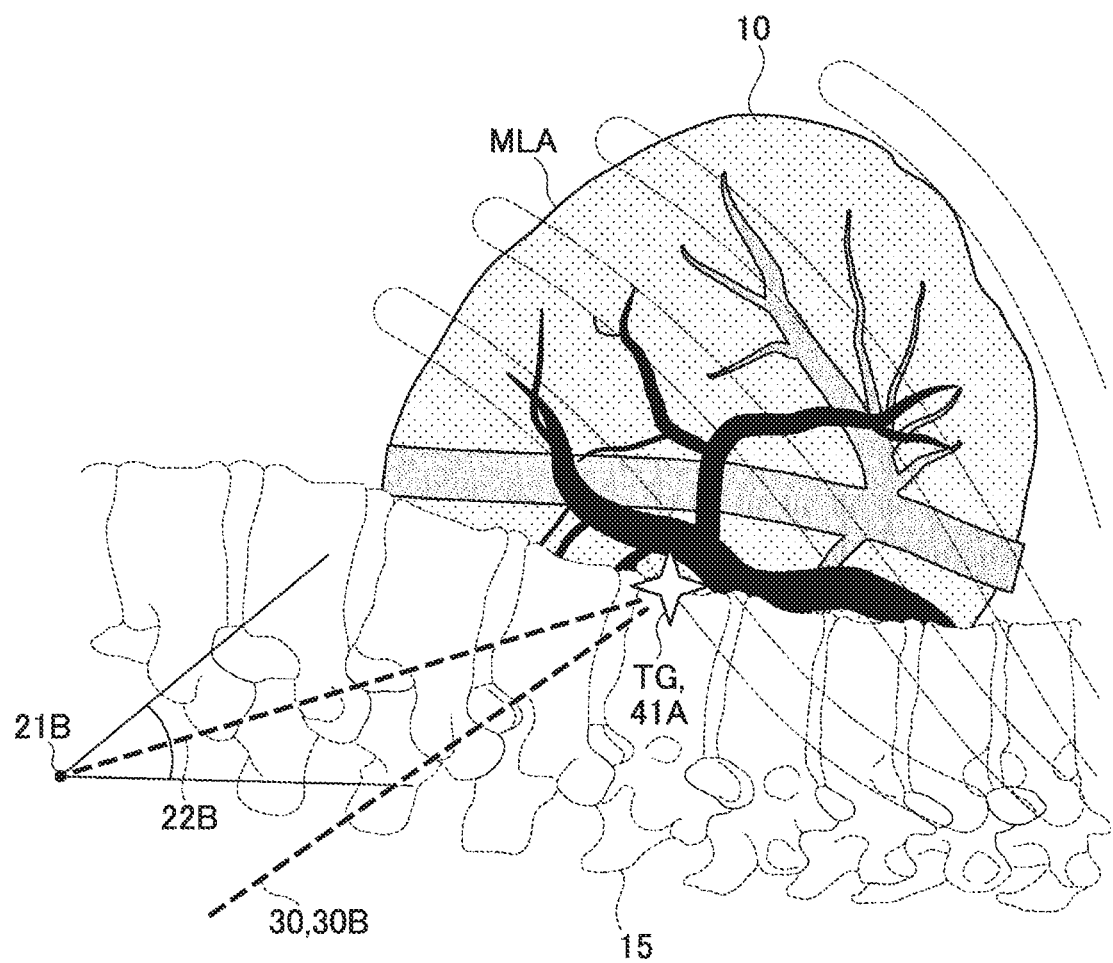
FIG. 8 is a schematic view illustrating an example of a virtual camera position.

FIG. 8 is a schematic view illustrating an example of the virtual camera position 21B.

The deformation processing unit 162 acquires the movement information and the rotation information of the target TG. In addition, the back calculation result of the movement information and the rotation information of the target TG is applied to the model ML before deformation, and the virtual camera position 21B and the virtual camera orientation 22B are calculated. In other words, the deformation processing unit 162 changes the position of the actual camera position 21A and the actual camera orientation 22A to the virtual camera position 21B and the virtual camera orientation 22B such that a relationship between the angle and the distance of the target position 41B and the target orientation 42B after deformation and the actual camera position 21A and the actual camera orientation 22A, and a relationship between the angle and the distance of the target position 41A and the target orientation 42A before deformation and the virtual camera position 21B and the virtual camera orientation 22B, become equal to each other, that is, the angles A1 and A2 are equal to each other. In this case, the deformation processing unit 162 may change the position and the orientation of the forceps 30 similar to a case of changing the camera position and the camera orientation. In other words, the position and the orientation of the actual forceps 30 (actual forceps 30A) may be changed to the position and the orientation of the virtual forceps 30 (virtual forceps 30B).

Next, a display example of an image by the medical image processing device 100 will be described.

Figure 9:
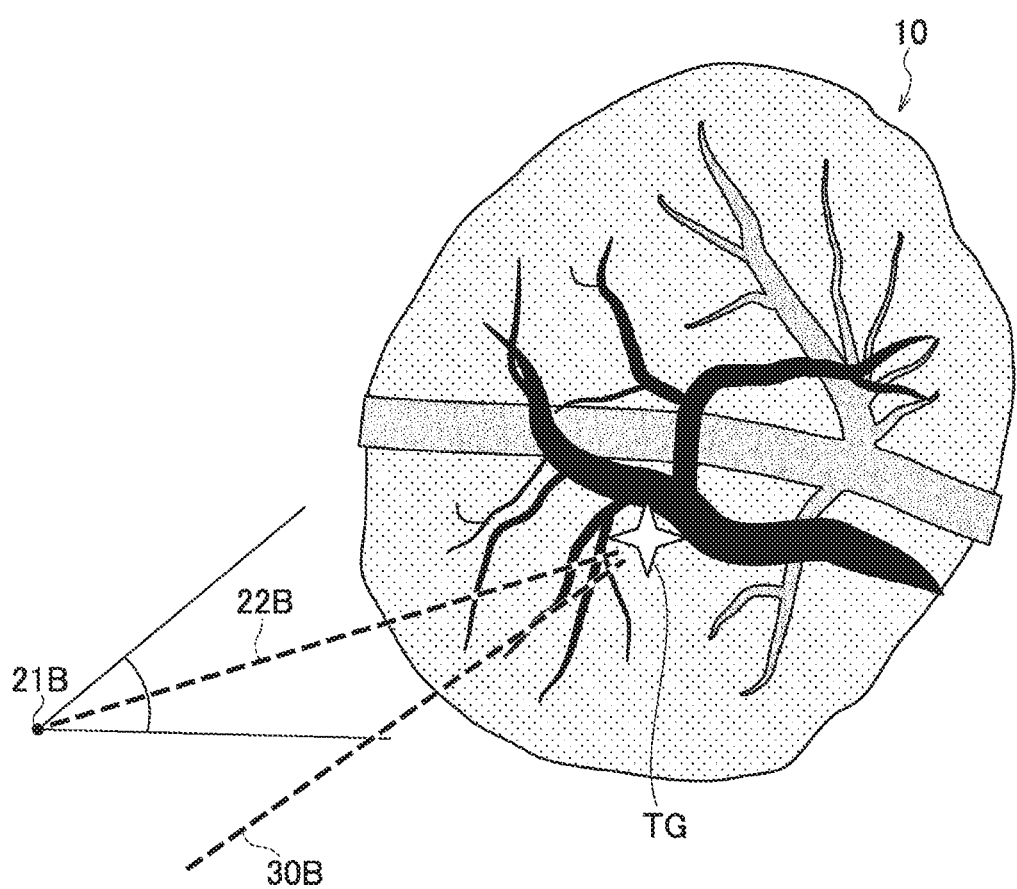
FIG. 9 is a view illustrating a display example of an image in which a body surface of an organ that does not include the target or an organ that includes the target are rendering targets.

As illustrated in FIG. 9, for example, the display controller 166 may hide the surface or the like of the organ (for example, bone) that does not include the target TG or the organ that includes the target TG, show the internal blood vessels, and show the rendered image. Accordingly, the medical image processing device 100 can suppress the presence of an obstacle in front of an image (for example, virtual endoscopic image) viewed from the virtual camera position 21B of which the camera has moved, and the target TG which is a target or the organs in the neighbor of the TG can be easily excellently observed.

Figure 10:
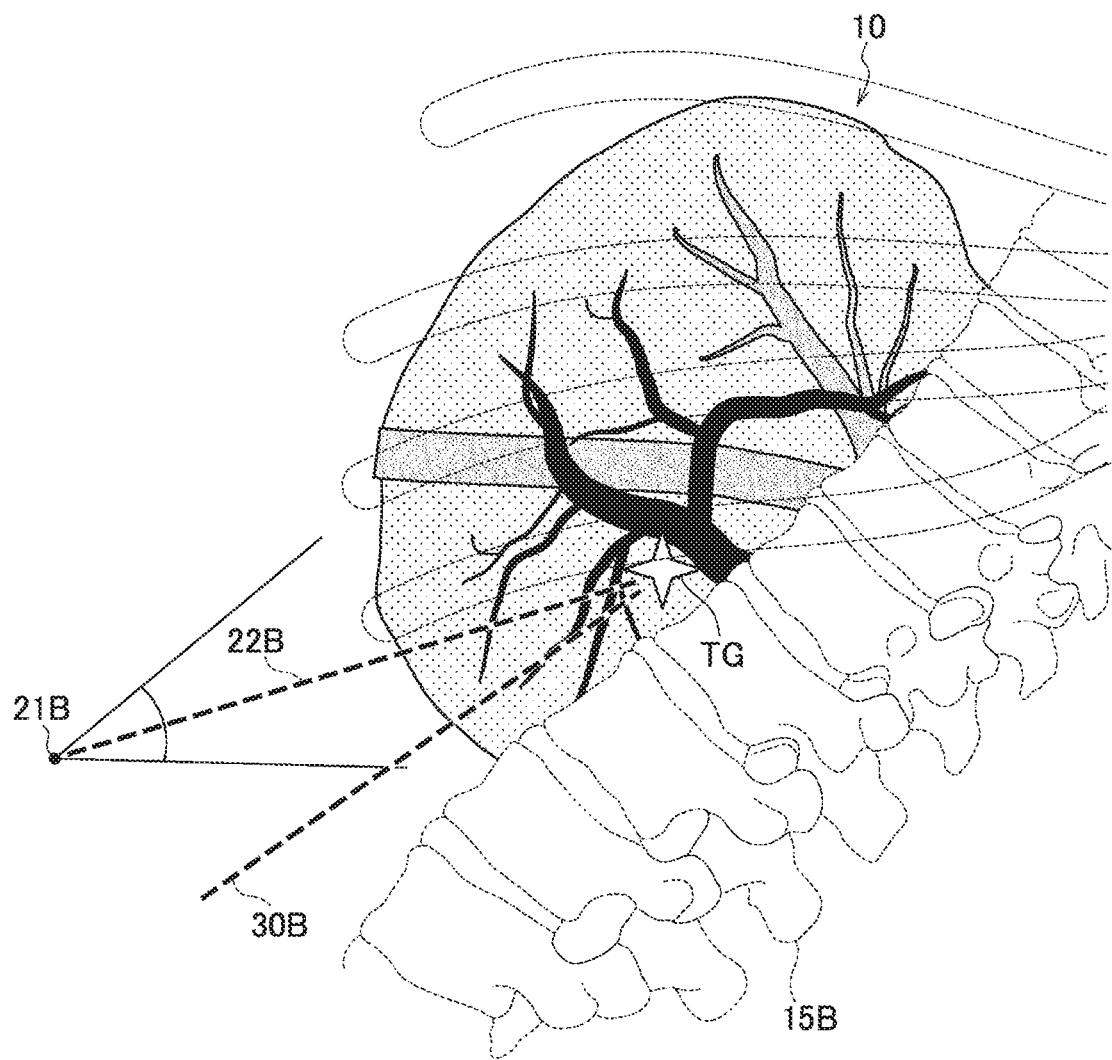
FIG. 10 is a view illustrating a display example of an image in which an organ that includes the target and a moved organ that does not include the target are rendering targets.

In addition, the image generator 165 may render an organ that does not include the target TG (for example, a bone or another organ that may interfere with surgery) separately from the organ that includes the target TG. As illustrated in FIG. 10, the display controller 166 may combine and show images of an organ that does not include the target TG and images of an organ that includes the target TG which are separately rendered.

In this case, the deformation processing unit 162 may move the separately rendered organ that does not include the target TG as the virtual camera position 21B moves from the actual camera position 21A. For example, similarly to a case of deriving the virtual camera position 21B and the virtual camera orientation 22B, the movement information and the rotation information of the target TG before and after deformation of the model ML may be back-calculated, and the position and orientation of the organ that does not include the target TG may be calculated. In this case, the position and the orientation of the organ that does not include the target TG before movement may be changed to the position and the orientation of the organ that does not include the target TG after movement such that the relationship between the angle and the distance of the target position 41B and the target orientation 42B after deformation and the position and the orientation of the organ that does not include the target TG before movement and the relationship between the angle and the distance of the target position 41A and the target orientation 42A before deformation and the position and the orientation of the organ that does not include target TG after movement become equal to each other. FIG. 10 illustrates an example of an image obtained by moving a bone 15 so as to become a bone 15B and rendering the bone 15B separately from the liver 10.

Figure 11:
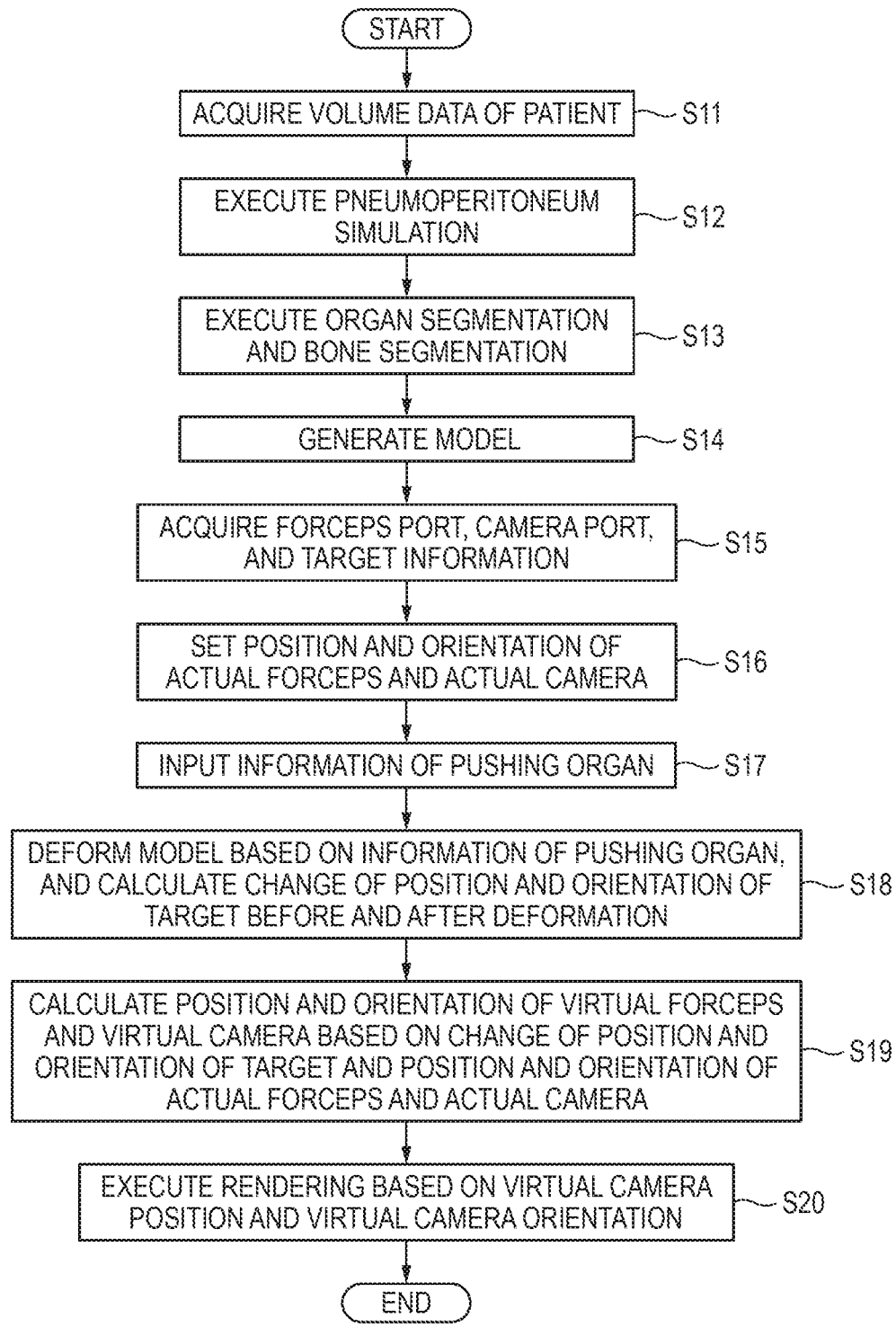
FIG. 11 is a flowchart illustrating an operation example of the medical image processing device.

FIG. 11 is a flowchart illustrating an operation example of the medical image processing device 100.

First, the volume data of the subject (for example, a patient) is acquired (S11). The pneumoperitoneum simulation is executed (S12). An organ segmentation for extracting an organ and a bone segmentation for extracting a bone are executed (S13). The model ML is acquired based on the volume data (S14). The forceps port, the camera port, and the target information (for example, the target position 41 and the target orientation 42) are acquired (S15). Information on the position (actual forceps position) and the orientation (actual forceps orientation) of the actual forceps, the position (actual camera position 21A) and the orientation (actual camera orientation 22A) of the actual camera is acquired (S16). In S16, the acquisition of the information of the actual camera position 21A and the actual camera orientation 22A may be the acquisition of the actual imaging range (actual view).

Information of pushing the organ that includes the target TG by the forceps 30 is acquired (S17). The model ML is deformed based on the information of pushing the organ, and the changes of the target position 41 and the target orientation 42 before and after deformation of the model ML are calculated (S18). Here, the target position 41B and the target orientation 42B after deformation may be calculated. Based on the changes of the target position 41 and the target orientation 42, the actual forceps position and the actual forceps orientation, and the actual camera position 21A and the actual camera orientation 22A, the position (virtual forceps position) and the orientation (virtual forceps orientation) of the virtual forceps 30B and the position (virtual camera position 21B) and the orientation (virtual camera orientation 22B) of the virtual camera after movement are calculated (S19). Based on the virtual camera position 21B and the virtual camera orientation 22B, rendered images are generated by viewing the volume data in the virtual camera orientation 22B from the virtual camera position 21B (S20). In addition, in S19 and S20, the calculation of the virtual camera position 21B and the virtual camera orientation 22B may be calculation of the virtual imaging range (virtual view), and image generation may be performed based on the virtual imaging range.

After the rendering in S20, the processing unit 160 may input the actual forceps position, the actual forceps orientation, the actual camera position, and the actual camera orientation in S16 via the UI 120, and perform the processing in S17 and subsequent steps. In other words, the processing of S16 to S20 may be repeated. Accordingly, the medical image processing device 100 can render and visualize the target TG in a state where the target TG is easily seen while reflecting the positions or the orientations of the operated forceps 30 or the camera even when the user freely moves and operates the forceps 30 or the camera.

After the rendering in S20, the processing unit 160 may input the information of pushing the organ in S17 via the UI 120, and perform the processing in S18 and subsequent steps. In other words, the processing of S17 to S20 may be repeated. Accordingly, the medical image processing device 100 can render and visualize the target TG in a state where the target TG is easily seen while reflecting the positions or the orientations of the operated forceps 30 or the camera, for example, even when the user moves the forceps 30 and changes the pushing method (for example, the position to press the organ, the pressing force, and the pressing direction) of the organ.

The accuracy of the organ segmentation and the bone segmentation in S13 may not be high. This is because, for example, even when there is some error in the contour of the organ or bone, it is sufficient when the situation of the target TG in the organ is easily visually recognized.

According to the processing of FIG. 11, the medical image processing device 100 can reduce the compute demand related to the deformation by deforming the model ML without deforming the volume data having a large number of pixels. In addition, a state where the organ is deformed by the deformation of the model ML and the target TG is visible can be easily reproduced without deforming the volume data to be visualized. Accordingly, the user can confirm whether or not the target TG can be approached from the actual camera position, whether or not there is an obstacle in the middle of the approach, whether or not the angle can be approached by the forceps 30, and the like. Further, in a case where the target TG cannot be visible even when the model ML is deformed, the medical image processing device 100 can recommend performing laparotomy instead of endoscopic surgery. In other words, it is possible to provide a material for determining whether endoscopic surgery is possible or laparotomy is necessary.

Although various embodiments have been described above with reference to the drawings, it is needless to say that the present disclosure is not limited to such examples. It is apparent to those skilled in the art that various changes or modifications can be conceived within the scope described in the claims, and naturally, those skilled in the art understand that the changes or modifications also belong to the technical scope of the present disclosure.

For example, the endoscopic surgery in which the preoperative simulation and the intraoperative navigation are performed may be laparoscopic surgery, arthroscopic surgery, bronchoscopic surgery, colonoscopic surgery, or other endoscopic surgery. The endoscopic surgery may be a surgery performed by an operator directly operating forceps, or may be a robot surgery using a surgical robot.

Deformation of tissue may also include excision of tissue. The deformation by excision here is performed on the model ML, but may also be applied to the volume data. This is because the compute demand related to excision is not enormous even when the volume data is used. Specifically, when the deformation processing unit 162 acquires an excision operation via the UI 120, for example, the deformation processing unit 162 may perform the deformation by the excision of the volume data in accordance with the excision operation. Further, the region processing unit 161 may set a cut location in the volume data as a non-masked region that is not a display target, and the display controller 166 may hide a part of the volume data included in the non-masked area.

Further, the deformation of the tissue may be represented by moving grid points arranged at equal intervals with respect to the volume data. In this case, the change in the orientation of the target can be represented by the change in the orientation of the line segment stretched between the grid points. For example, this implementation method is described in Reference Patent Literature 1.

(Reference Patent Literature 1: U.S. Pat. No. 8,311,300)

Regarding the movement of the camera, while the camera position (camera) can be moved with respect to the target TG before and after deformation, the distance may change without keeping the distance between the target TG and the camera position constant. For example, in a case where the organ including the target TG is visualized by the virtual endoscopic image (perspective projection image), the distance between the camera and the target TG may be maintained or may not be maintained in the virtual endoscopic image. In a case of parallel projection, it is difficult to consider the distance between the target TG and the camera. In a case where the distance is not maintained, for example, zoom-in and zoom-out different from the distance between the actual camera position and the target TG can be represented.

In addition, the deformation processing unit 162 may further change at least one of the virtual camera position and the virtual camera orientation via the UI 120 after the movement of the actual camera position and the actual camera orientation with respect to the target TG to the virtual camera position and the virtual camera orientation. Accordingly, the medical image processing device 100 can additionally perform manual eye movement in addition to automatic eye movement based on the positional relationship between the actual camera position and the target TG in the model ML after deformation. Therefore, for example, by finely adjusting the result of the automatic camera movement by manual camera movement and confirming the image generated with the manually moved camera as a reference, the situation of the target TG can be made easier to be seen.

Further, a case where the processing unit 160 visualizes the neighbor of target TG by moving from the actual camera position to the virtual camera position in a case where the target TG is difficult to be seen or invisible from the actual camera position, has been exemplified, but the present disclosure is not limited thereto. For example, although the target TG is visible from the actual camera position, the processing unit 160 may move the situation of the target TG to the virtual camera position that is easier to be seen, and visualize the situation of the neighbor of the target TG viewed from the virtual camera position. Accordingly, the medical image processing device 100 can more easily observe the situation of the target TG even in a case where the target TG is visible.

Although the liver is mainly illustrated as an organ to which the above-described embodiment is applied, other organs may be used. For example, the above-described embodiment may be applied to a lung, stomach, intestine, pancreas, or other organs.

In addition, the medical image processing device 100 may include at least the processor 140 and the memory 150. The acquisition unit 110, the UI 120, and the display 130 may be external to the medical image processing device 100.

Further, it is exemplified that the volume data as the captured CT image is transmitted from the CT scanner 200 to the medical image processing device 100. Instead of this, the volume data may be transmitted to and stored in a server on the network (for example, an image data server (PACS) (not illustrated)) or the like such that the volume data is once stored. In this case, the acquisition unit 110 of the medical image processing device 100 may acquire the volume data from a server or the like via a wired circuit or a wireless circuit when necessary, or may acquire the volume data via any storage medium (not illustrated).

Further, it is exemplified that the volume data as the captured CT image is transmitted from the CT scanner 200 to the medical image processing device 100 via the acquisition unit 110. This also includes a case where the CT scanner 200 and the medical image processing device 100 are established by being substantially combined into one product. In addition, this also includes a case where the medical image processing device 100 is handled as the console of the CT scanner 200.

Further, although it is exemplified that the CT scanner 200 is used to capture an image and the volume data including information on the inside of the subject is generated, the image may be captured by another device to generate volume data. Other devices include magnetic resonance imaging (MRI) devices, positron emission tomography (PET) devices, blood vessel imaging devices (angiography devices), or other modality devices. In addition, the PET device may be used in combination with other modality devices.

Further, a medical image processing method in which the operation in the medical image processing device 100 is defined can be expressed. In addition, a program for causing a computer to execute each step of the medical image processing method can be expressed.

(Overview of Above-Described Embodiment)

According to one aspect of the above-described embodiments, there is provided the medical image processing device 100 (an example of an endoscopic surgery support apparatus) that supports the endoscopic surgery, including the acquisition unit 110 and the processing unit 160. The acquisition unit 110 has a function of acquiring the volume data of the subject. The processing unit 160 sets the model ML that represents the tissue included in the volume data. The processing unit 160 sets an actual view (an example of the first view) for visualizing the volume data and the position of the target TG in the model ML. The processing unit 160 acquires information (an example of first operation information) of the deforming operation for deforming the model ML. The processing unit 160 may calculate the change in the position and the orientation of the target TG before and after deformation of the model ML based on the information on the deforming operation. The processing unit 160 may use the calculated change in the position and orientation of the target TG to calculate the virtual view such that the position and the orientation of the target TG after change with respect to the actual view and the position and the orientation of the target TG before change with respect to the virtual view (an example of the second view) are equal to each other. The processing unit 160 may visualize the volume data based on the virtual view.

Accordingly, the medical image processing device 100 can obtain the virtual view such that the positional relationship between the target TG and the actual camera after deformation is similar to the positional relationship between the target TG and the virtual camera before deformation without performing deformation of the tissues, and provide the visualization of the volume data based on the virtual view. Accordingly, for example, when the orientation of actual line of sight is viewed from the actual view, even in a case where the target is positioned behind the organ, not by the visualization by deforming the organ but by the visualization of the organ that is not deformed by changing the view, it is possible to represent a state similar to that visualized by deforming the organ. Moreover, since the volume data is not deformed, the compute demand can be reduced. Furthermore, it is not necessary to appropriately set the rigidity for each voxel of the volume data, and to consider the slippage at the boundary of the organ, the flow of body fluid, and the air. Further, in a case where the organ is repeatedly deformed little by little considering a surgery process, it is not necessary to maintain the consistency of the volume data related to the deformation processing. Therefore, manual fine adjustment of the volume data and the ROI also becomes unnecessary. Therefore, for example, it is possible to perform a real-time simulation in which an operator operates an organ using the forceps 30 in the endoscopic surgery. In particular, it is ensured that the organ boundaries are not broken.

Further, since the visualized organ is not deformed, the deformation of the organ does not cause a plurality of organs to overlap each other in the virtual space. In addition, since the visualized organs are not deformed, for example, even in a case where the segmentation of each organ is incorrect, it is possible to clearly visualize the blood vessels that are connected to the contour of the liver and the blood vessels that are not connected, and to suppress deterioration of the accuracy of surface rendering. In this manner, the visualization of the target in the subject can be improved.

Further, the processing unit 160 may segment the tissue including the target TG in the subject and set the model ML based on the segmented tissue. Accordingly, the medical image processing device 100 can visualize the volume data viewed from the virtual view by using the model ML only for the tissue including the target TG, and can easily observe the tissue including the target TG. Even in this case, in the medical image processing device 100, since the visualized organs are not deformed, the deformed organs and the organs that are not deformed do not coexist, and it is possible to prevent the deformation of the organs from causing a plurality of organs to overlap each other in the virtual space. Further, it becomes easy to perform the deforming operation on a model corresponding to an organ that is closely related to the target TG.

Further, the processing unit 160 may cause the display 130 (an example of the display unit) to show information indicating the contour of the tissue. Then, in accordance with the deformation of the model ML, the contour may be deformed and the information indicating the contour may be shown. Although there are also organs of which the contours are not clear, the medical image processing device 100 can clarify the shape of the tissue by showing the information indicating the contours. The model ML for the deforming operation may also be shown on the display 130. The contour may be generated by a polygon.

Further, the processing unit 160 may hide the bone of the subject in the visualization of the volume data based on the virtual view. Accordingly, the medical image processing device 100 can exclude information that is not directly related to an organ that includes the target from the display target, and can make the target easy to be seen.

Further, in the visualization of the volume data based on the virtual view, the processing unit 160 may show the bone of the subject included in the image visualized in a case of visualizing the volume data based on the actual view. Accordingly, the medical image processing device 100 can visualize the target TG and the bone in the neighbor of the target TG, and can support the endoscopic surgery by the operator. In addition, the processing unit 160 may visualize the bone without extracting the bone. For example, since the CT value of the bone is higher than that of other tissues, the bone can be visualized by visualizing voxels at which a CT value is equal to or greater than a threshold value.

Further, the processing unit 160 may show the forceps 30 inserted toward the target TG inside the subject together with the volume data. Accordingly, the medical image processing device 100 can visualize the positional relationship between the target TG and the forceps 30 for performing various measures with respect to the target TG, and can support the endoscopic surgery by the operator.

Further, the processing unit 160 may acquire information (an example of second operation information) on the deforming operation for operating the distance between the target position 41A before deformation of the model and the virtual camera corresponding to the virtual view. Then, the volume data may be visualized based on the information on the deforming operation. Accordingly, the medical image processing device 100 can adjust the virtual camera by manually moving the camera, and can visualize the target TG at a distance or an angle from the virtual camera desired by the operator. Therefore, an image that includes the target TG desired by the operator can be easily obtained.

According to an aspect of the above-described embodiment, there is provided an endoscopic surgery support method including: a step of acquiring volume data of a subject; a step of setting a model that represents a tissue included in the volume data; a step of setting a first view for visualizing the volume data and a position of a target in the model; a step of acquiring first operation information for deforming the model; a step of calculating change in position and an orientation of the target before and after deformation of the model, based on the first operation information; a step of calculating, using the calculated change in the position and the orientation of the target, a second view such that the position and the orientation of the target after the change with respect to the first view and the position and the orientation of the target before the change with respect to the second view become equal to each other; and a step of visualizing the volume data based on the second view.

According to another aspect of the present embodiment, there is provided a program for causing a computer to execute the endoscopic surgery support method.

In the present disclosure, an endoscopic surgery support apparatus, an endoscopic surgery support method, and an endoscopic surgery support system that are capable of improving visualization of a target in a subject is described.

What is claimed is:

1. An endoscopic surgery support apparatus for supporting endoscopic surgery, comprising:
an acquisition circuit; and
a processing circuit configured to:
acquire volume data of a subject;
set a model that represents a tissue included in the volume data;
set a first camera position and a first camera orientation for visualizing the volume data and a position of a target in the model;
acquire first operation information for deforming the model;
calculate change in the position and an orientation of the target due to deformation of the model, based on the first operation information;
calculate, using the calculated change in the position and the orientation of the target, a second camera position and a second camera orientation, such that (i) the position and the orientation of the target after the change with respect to the first camera position and the first camera orientation and (ii) the position and the orientation of the target before the change with respect to the second camera position and the second camera orientation become equal to each other; and
visualize the volume data based on the second camera position and the second camera orientation.

2. The endoscopic surgery support apparatus according to claim 1, wherein the processing circuit is configured to segment a tissue that includes the target and is in the subject, and is configured to set the model based on the segmented tissue.

3. The endoscopic surgery support apparatus according to claim 2, wherein the processing circuit is configured to:
show a contour of the tissue on a display unit; and
deform the contour in accordance with the deformation of the model.

4. The endoscopic surgery support apparatus according to claim 1, wherein the processing circuit is configured to hide a bone of the subject when visualizing the volume data.

5. The endoscopic surgery support apparatus according to claim 1, wherein the processing circuit is configured to show a bone of the subject in an image of the volume data that is visualized with respect to the first camera position and the first camera orientation while visualizing the rest of the volume data with respect to the second camera position and the second camera orientation.

6. The endoscopic surgery support apparatus according to claim 1, wherein the processing circuit is configured to show, together with the volume data, forceps inserted toward the target inside of the subject.

7. The endoscopic surgery support apparatus according to claim 1, wherein the processing circuit is configured to:
acquire second operation information for operating a distance between the position of the target and a camera corresponding to the second camera position and the second camera orientation before the deformation of the model, and
visualize the volume data based on the second operation information.

8. An endoscopic surgery support method comprising:
acquiring volume data of a subject;
setting a model that represents a tissue included in the volume data;
setting a first camera position and a first camera orientation for visualizing the volume data and a position of a target in the model;
acquiring first operation information for deforming the model;
calculating change in position and an orientation of the target due to deformation of the model, based on the first operation information;
calculating, using the calculated change in the position and the orientation of the target, a second camera position and a second camera orientation, such that (i) the position and the orientation of the target after the change with respect to the first camera position and the first camera orientation and (ii) the position and the orientation of the target before the change with respect to the second camera position and the second camera orientation become equal to each other; and
visualizing the volume data based on the second camera position and the second camera orientation.

9. An endoscopic surgery support system for supporting endoscopic surgery, comprising:
an acquisition circuit; and
a processing circuit configured to:
acquire volume data of a subject;
set a model that represents a tissue included in the volume data;
set a first camera position and a first camera orientation for visualizing the volume data and a position of a target in the model;
acquire first operation information for deforming the model;
calculate change in the position and an orientation of the target due to deformation of the model, based on the first operation information;
calculate, using the calculated change in the position and the orientation of the target, a second camera position and a second camera orientation, such that (i) the position and the orientation of the target after the change with respect to the first camera position and the first camera orientation and (ii) the position and the orientation of the target before the change with respect to the second camera position and the second camera orientation become equal to each other; and
visualize the volume data based on the second camera position and the second camera orientation.

* * * * *